United States Patent [19]
Goda et al.

[11] Patent Number: 5,932,731
[45] Date of Patent: Aug. 3, 1999

[54] PROCESS FOR PREPARING AROMATIC OR HETEROAROMATIC SULFUR COMPOUND

[75] Inventors: Hiroshi Goda; Mikio Yamamoto; Jun-ichi Sakamoto; Hitoshi Karino, all of Hyogo-ken, Japan

[73] Assignee: Sumitomo Seika Chemicals Co., Ltd., Hyogo-ken, Japan

[21] Appl. No.: 08/996,074

[22] Filed: Dec. 22, 1997

Related U.S. Application Data

[62] Division of application No. 08/687,556, Jul. 24, 1996, Pat. No. 5,741,933.

[30] Foreign Application Priority Data

Nov. 24, 1994 [JP] Japan .................................. 6-289763

[51] Int. Cl.$^6$ ...................... C07D 241/18; C07D 213/28; C07D 239/36; C07D 231/18
[52] U.S. Cl. .......................... 544/408; 546/290; 546/303; 548/213; 548/225; 548/243; 548/366.1; 548/263.2; 548/484; 549/33; 549/62; 549/466; 549/475
[58] Field of Search ..................... 546/290, 303; 548/182, 213, 366.1, 263.2, 225, 541, 484; 213/243; 549/33, 62, 466, 475; 544/408

[56] References Cited

U.S. PATENT DOCUMENTS

4,868,336  9/1989  Presnall ..................................... 568/25

FOREIGN PATENT DOCUMENTS

| 2424248A1 | 5/1974 | Germany . |
| 60-199871 | 10/1985 | Japan . |
| 62-201862 | 9/1987 | Japan . |
| 1-165570 | 6/1989 | Japan . |

OTHER PUBLICATIONS

Adams et al., "Thioethers, III. Preparation of Aromatic Di- and Tri–mercapto Compounds by Dealkylation of Ary Alkyl Thioethers." *J. Am Chem. Soc.*, 81:4939(1959).

Ferretti, "1.2.–Dimercaptobenzene," *Org. Synth. Coll.* 5:419(1973).

Testaferri et al., "A Convenient Synthesis of Aromatic Thiols from Unactivated Aryl Halids," *Tetrahedron Letters.* 21:3099(1980).

Tiecco et al., "Selective Dealkylation of Bis[alkylthiol] benzenes; Elimination–Substitution Competition with Methoxide and Methanethiolate Ions in Hexamethylphosphoric Triamide." *Synthesis.* p. 478 Jun. 1982).

Young et al., "Methyl Group as a Protecting Group for Arylthiols; A Mild and Efficient Method for the Conversion of Methyl Acryl Sulfides to Arylthiols." *Tetrahedron Letters.* 25:1753(1984).

*Primary Examiner*—Alan L. Rotman
*Attorney, Agent, or Firm*—Knobbe, Martens Olson & Bear, LLP

[57] ABSTRACT

The present invention provides a process for preparing an aromatic or heteroaromatic thiol represented by the formula (2), the process comprising hydrolyzing an aromatic or heteroaromatic halogenated methyl sulfide represented by the formula (1)

$$Ar\text{-}(SCH_{3-m}X_m)_n \quad (1)$$

$$Ar\text{-}(SH)_n \quad (2)$$

wherein Ar is an aromatic or heteroaromatic ring which has no substituent or which has an optional substituent or substituents, X is a halogen atom, m is an integer of 1 to 3 and n is 1 or 2.

23 Claims, No Drawings

PROCESS FOR PREPARING AROMATIC OR HETEROAROMATIC SULFUR COMPOUND

CROSS-REFERENCE

This application is a divisional of Ser. No. 08/687,556 filed Jul. 24, 1996, now U.S. Pat. No. 5,741,933, which is a §371 of PCT/JP95/02315 filed Nov. 13, 1995.

FIELD OF THE INVENTION

The present invention relates to a novel process for preparing an aromatic or heteroaromatic thiol or an aromatic or heteroaromatic disulfide and a novel process for preparing an aromatic or heteroaromatic halogenated methyl sulfide which is useful as the starting material for said thiol or disulfide. The aromatic or heteroaromatic thiol and disulfide are useful compounds which are used for various purposes as in pharmaceutical compositions, agricultural compositions, functional materials or the like.

BACKGROUND ART

Various processes have been known for preparing an aromatic or heteroaromatic thiol or disulfide. Among them, the conventional processes for preparing an aromatic or heteroaromatic thiol by bond cleavage in alkyl sulfide are classified into the following three processes:

(A) Process comprising reacting an aromatic alkyl sulfide with alkyl thiolate in hexamethylphosphoric triamide (abbreviation HMPA) used as a solvent (Tetrahedron Letters 21 3099 (1980))
(Synthesis Communications 478 (1982))

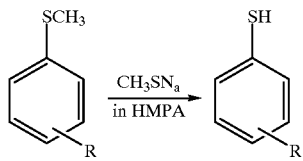

(B) Process comprising reacting an aromatic alkyl sulfide with metal sodium in liquid ammonia
(Org. Synth. Coll. Vol. 5 419 (1973))
(J. Am. Chem. Soc. 81 4939 (1959))

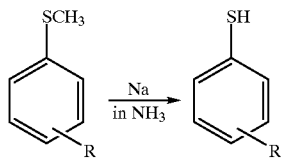

(C) Process comprising oxidizing an aromatic methyl sulfide with perbenzoic acid, reacting the oxide with trifluoroacetic acid, and causing triethylamine to act on the reaction mixture (Tetrahedron Letters 25 1753 (1984))

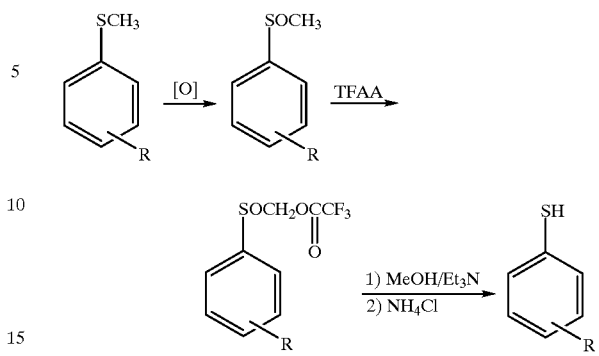

However, these conventional processes pose the following drawbacks when commercially conducted.

The process (A) is defective in that the HMPA used as a solvent is not easily available and expensive and that the sodium mercaptide used as a reagent is difficult to handle in a nonaqueous system. Further problematic is the disposal of dialkyl sulfide produced as a by-product.

The process (B) is industrially difficult to carry out because of high risks involved in handling, use of an expensive metal sodium and low-yield production. The process (C) requires a number of reaction procedures and necessitates the use of an expensive, highly dangerous reaction reagent such as perbenzoic acid, trifluoroacetic acid, etc.

As described above, none of the conventional processes for preparing an aromatic or heteroaromatic thiol by bond cleavage in alkyl sulfide are satisfactory from the viewpoint of industrial application.

DISCLOSURE OF THE INVENTION

An object of the present invention is to provide a process for preparing an aromatic or heteroaromatic thiol at a commercially low cost and with ease.

Another object of the invention is to provide a process for preparing an aromatic or heteroaromatic disulfide at a commercially low cost and with ease.

The present inventors conducted extensive research on the reaction for bond cleavage in alkyl sulfide to overcome the drawbacks of said known processes and to provide processes for preparing aromatic or heteroaromatic thiol and disulfide at commercially low costs and with ease.

The inventors' research found that the aromatic or heteroaromatic halogenated methyl sulfide represented by the formula (1) can be easily hydrolyzed to give the corresponding aromatic or heteroaromatic thiol represented by the formula (2) in a high yield. The finding led to the completion of the present invention. Stated more specifically, the first invention is directed to a process for preparing an aromatic or heteroaromatic thiol represented by the formula (2), the process comprising hydrolyzing an aromatic or heteroaromatic halogenated methyl sulfide represented by the formula (1) as shown below:

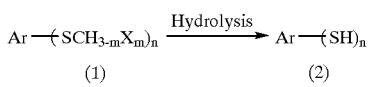

wherein Ar is an aromatic or heteroaromatic ring which has no substituent or which has an optional substituent or substituents, X is a halogen atom, m is an integer of 1 to 3 and n is 1 or 2.

Since thiol can be easily converted to disulfide by oxidation, the corresponding disulfide can be produced by executing an oxidation step subsequent to the above-mentioned reaction step. The second invention is directed to a process for preparing an aromatic or heteroaromatic disulfide represented by the formula (3), the process comprising the steps of hydrolyzing an aromatic or heteroaromatic halogenated methyl sulfide represented by the formula (1), and oxidizing the reaction mixture as shown below:

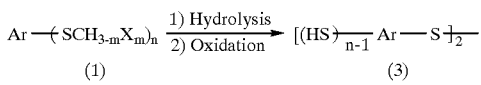

wherein Ar is an aromatic or heteroaromatic ring which has no substituent or which has an optional substituent or substituents, X is a halogen atom, m is an integer of 1 to 3 and n is 1 or 2.

The present invention will be described below in more detail.

The contemplated aromatic or heteroaromatic thiol represented by the formula (2) is prepared in high yields by hydrolyzing an aromatic or heteroaromatic halogenated methyl sulfide represented by the formula (1).

In the formulas, the aromatic or heteroaromatic rings represented by Ar are not specifically limited and include a wide variety of aromatic or heteroaromatic rings which have no substituent or which have an optional substituent or substituents. Examples of the aromatic or heteroaromatic ring represented by Ar are a benzene ring, naphthalene ring, pyridine ring, pyrazole ring, pyrazine ring, triazole ring, oxazole ring, isooxazole ring, thiazole ring, isothiazole ring, thiophene ring, benzothiophene ring, furan ring, benzofuran ring, pyrrole ring, indole ring, etc.

Examples of optional substituents are halogen, cyano, formyl, amino, carboxyl or its ester, carbamoyl, alkyl carbonyl, nitro, sulfonic acid, alkyl, alkoxyl, hydroxyl, substituted phenylthio, etc.

Among the aromatic or heteroaromatic rings represented by Ar, preferred are a benzene ring, pyridine ring, thiazole ring, and isothiazole ring which have an optional substituent or substituents, and more preferred are benzene rings each having, in an optional position or positions, halogen, cyano, formyl, amino, carboxyl or its ester, carbamoyl, alkyl carbonyl, nitro, sulfonic acid, alkyl, alkoxyl, hydroxyl or substituted phenylthio.

In the aromatic or heteroaromatic halogenated methyl sulfide represented by the formula (1), X is chlorine, bromine or iodine and m is 1, 2 or 3. Among these substances, chlorine is preferred as X. For hydrolysis to make smooth progress, desirably m is 2 or 3 or a mixture of sulfides wherein m is 2 or 3 is used.

The hydrolysis takes place and proceeds merely by adding water and heating, thereby producing the desired aromatic or heteroaromatic thiol of the formula (2). The hydrolysis reaction makes smooth progress if effected in the presence of an acid. While such acids are not specifically limited, mineral acids such as hydrochloric acid, sulfuric acid, nitric acid and phosphoric acid are used for economical advantage. Among them, hydrochloric acid and sulfuric acid are more preferred. The acid is sufficient if its amount is 0.01 to 1 times the weight of halogenated methyl sulfide of the formula (1).

In this case, the addition of an alcohol, particularly a lower alcohol, causes the hydrolysis reaction to more smoothly proceed. Examples of useful lower alcohols are methanol, ethanol, isopropanol, n-propanol, isobutanol, n-butanol, sec-butanol, etc. Among them, methanol is preferred from an economical viewpoint. The amount of the alcohol, although not specifically limited, is usually 0.5 to 10 times the weight of halogenated methyl sulfide of the formula (1).

Useful solvents are not specifically limited and even said reaction proceeds without a solvent. Examples of useful solvents are hydrocarbons such as hexane, cyclohexane and heptane, halogenated hydrocarbons such as dichloroethane, dichloromethane and chloroform, aromatic hydrocarbons such as benzene, toluene, xylene, chlorobenzene, dichlorobenzene and trichlorobenzene. The amount of the solvent used is not specifically limited but is usually 0.1 to 10 times the weight of the halogenated methyl sulfide of the formula (1).

The reaction temperature is usually in a range of about 20 to about 100° C., preferably about 50 to about 90° C. Too low a reaction temperature retards the reaction, whereas too high a reaction temperature causes a side reaction, which results in the decrease of yields. The reaction time is usually in a range of about 1 to about 10 hours.

The aromatic or heteroaromatic thiol produced according to the present invention can be isolated by conventional distillation or crystallization.

The aromatic or heteroaromatic thiols obtainable in the present invention include various compounds such as thiophenol, 4-chlorothiophenol, 2-chlorothiophenol, 2,4-dichlorothiophenol, 2,5-dichlorothiophenol, 3,5-dichlorothiophenol, 2,6-dichlorothiophenol, 4-bromothiophenol, 2,4-dibromothiophenol, 1,4-benzenedithiol, 1,2-benzenedithiol, 4-butyl-1,2-benzenedithiol, 4-cyanothiophenol, 2-cyanothiophenol, 4-methylthiophenol, 2-methylthiophenol, 4-hydroxythiophenol, 2-hydroxythiophenol, 4-acetylthiophenol, 4-nitrothiophenol, 2-nitrothiophenol, 4-aminothiophenol, 2-aminothiophenol, 4-mercaptobenzoic acid, 2-mercaptobenzoic acid, 2-formylthiophenol, 4-formylthiophenol, 4-mercaptobenzenesulfonic acid, 2-cyano-3-chlorothiophenol, 4-carbamoylthiophenol, 4,4'-thiodibenzenethiol, 4,4'-oxydibenzenethiol, 4-(phenylthio)benzenethiol, 4-(phenylsulfonyl)benzenethiol, 2-pyridinethiol, 4-pyridinethiol, 2-mercaptothiophene, 2,6-dimercaptothiophene, 1-naphthalenethiol, 2-naphthalenethiol, 2-mercaptopyrazine, 4-mercaptotriazole, 5-mercaptotriazole, 2-mercaptooxazole, 4-mercaptooxazole, 4-mercaptoisooxazole, 2-mercaptothiazole, 4-mercaptothiazole, and 4-mercaptoisothiazole.

To obtain the aromatic or heteroaromatic disulfide of the formula (3) as the contemplated product, the object can be easily accomplished by additionally executing an oxidation step after said hydrolysis reaction. In other words, this can be done by adding an oxidizer after the hydrolysis.

A specific oxidizer is not necessary and conventional known oxidizers can be used. Oxidation methods employable herein are oxygen oxidation, air oxidation, oxidation involving a halogen such as chlorine, and bromine, oxidation involving a peroxide such as hydrogen peroxide and peracetic acid, and oxidation involving an alkali metal salt of hypohalous acid such as sodium hypochlorite and sodium hypobromite.

The reaction temperature is variable depending on the oxidation method, and can not be specifically defined. It is usually in a range of about 0 to about 100° C., preferably about 30 to about 90° C. Too low a reaction temperature results in the reduction of reaction rate, whereas too high a reaction temperature gives rise to a side reaction, thereby lowering the yield. The reaction time is usually in a range of about 0.5 to about 15 hours.

The aromatic or heteroaromatic disulfide thus formed can be easily isolated by crystallization or the like.

The aromatic or heteroaromatic disulfide produced by the present invention includes a disulfide derived from said aromatic or heteroaromatic thiol.

As stated above, the aromatic or heteroaromatic thiol represented by the formula (2) can be easily prepared by hydrolyzing the aromatic or heteroaromatic halogenated methyl sulfide represented by the formula (1), and the aromatic or heteroaromatic disulfide represented by the formula (3) can be easily prepared by hydrolyzing the aromatic or heteroaromatic halogenated methyl sulfide represented by the formula (1), followed by oxidation.

The aromatic or heteroaromatic halogenated methyl sulfide of the formula (1) to be used herein can be produced by halogenating the corresponding aromatic or heteroaromatic methyl sulfide represented by the formula (4) (the third invention of the present application).

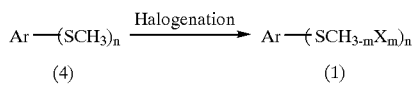

wherein Ar is an aromatic or heteroaromatic ring which has no substituent or which has an optional substituent or substituents, X is a halogen atom, m is an integer of 1 to 3 and n is 1 or 2.

When the aromatic or heteroaromatic halogenated methyl sulfide of the formula (1) is prepared by halogenating the aromatic or heteroaromatic methyl sulfide of the formula (4), chlorine, sulfuryl chloride, bromine, sulfuryl bromide, etc. can be used as a halogenating agent. Among them, chlorine is preferred from an economical viewpoint.

The aromatic or heteroaromatic halogenated methyl sulfide of the formula (1) is a compound wherein m is 1, 2 or 3. If the compound of the formula (1) wherein m is 2 or 3, or a mixture of these compounds is used, the hydrolysis reaction in the subsequent step can proceed smoothly.

The amount of the halogenating agent to be used is 1.5 to 7 moles, preferably 2 to 5 moles, per mole of the aromatic or heteroaromatic methyl sulfide of the formula (4).

Useful solvents are not specifically limited and even said reaction proceeds without a solvent. Examples of useful solvents are hydrocarbons such as hexane, cyclohexane and heptane, halogenated hydrocarbons such as dichloroethane, dichloromethane and chloroform, and aromatic hydrocarbons such as benzene, toluene, xylene, chlorobenzene, dichlorobenzene and trichlorobenzene. The amount of the solvent used is not specifically limited but is usally 0.1 to 10 times the weight of aromatic or heteroaromatic methyl sulfide of the formula (4).

The halogenation reaction temperature is usually in a range of about −20 to about 100° C., preferably about −5 to about 60° C., although variable with the contemplated compound. Too low a reaction temperature retards the reaction, whereas too high a reaction temperature brings about a side reaction, which leads to the decrease of the yield.

The aromatic or heteroaromatic halogenated methyl sulfide of the formula (1) thus formed can be isolated by conventional distillation or crystallization.

To obtain the aromatic or heteroaromatic thiol of the formula (2), or the aromatic or heteroaromatic disulfide of the formula (3) as the contemplated product, the reaction mixture of the halogenation reaction itself can be used in the subsequent hydrolysis reaction or oxidation reaction further to hydrolysis reaction without isolation of the aromatic or heteroaromatic halogenated methyl sulfide of the formula (1).

In other words, the present invention provides a process for preparing the aromatic or heteroaromatic thiol of the formula (2), the process comprising the steps of halogenating the aromatic or heteroaromatic methyl sulfide of the formula (4) to give the aromatic or heteroaromatic halogenated methyl sulfide of the formula (1), and hydrolyzing the compound of the formula (1) (the fourth invention of the present application).

Also the present invention provides a process for preparing the aromatic or heteroaromatic disulfide of the formula (3), the process comprising the steps of halogenating the aromatic or heteroaromatic methyl sulfide of the formula (4) to give the aromatic or heteroaromatic halogenated methyl sulfide of the formula (1), subsequently hydrolyzing the compound of the formula (1) and further oxidizing the hydrolyzate (the fifth invention of the present application).

In these processes, by combining said reactions, the aromatic or heteroaromatic thiol of the formula (2) or the aromatic or heteroaromatic disulfide of the formula (3) is produced from the aromatic or heteroaromatic methyl sulfide of the formula (4) in one pot in a high yield.

The present invention provides a novel process for preparing an aromatic or heteroaromatic thiol or disulfide which is used for various applications as in pharmaceutical compositions, agricultural compositions, functional materials or the like and a novel process for preparing an aromatic or heteroaromatic halogenated methyl sulfide useful as the starting material for preparing said thiol or disulfide. According to the processes of the present invention, the end product can be simply prepared in high yields by halogenating, hydrolyzing and oxidizing a commercially available aromatic or heteroaromatic methyl sulfide. Thus the processes of the present invention have pronouncedly high economical and commercial values.

BEST MODE FOR CARRYING OUT THE INVENTION

The present invention will be described below in more detail with reference to Examples to which the present invention is not limited at all.

EXAMPLE 1

A 1-liter, 4-necked flask equipped with a stirrer, thermometer, condenser and gas inlet tube was charged with 227.5 g (1.00 mole) of 4-chlorophenyl dichloromethyl sulfide, 50 g of water and 400 g of methanol. The mixture was heated to 70° C. for 5 hours to complete hydrolysis. After completion of the reaction, water was added to separate the oil layer. Then distillation gave 136.5 g of 4-chlorothiophenol. The yield based on 4-chlorophenyl dichloromethyl sulfide was 94.5%.

EXAMPLES 2 TO 42

The same procedure as in Example 1 was carried out with exception of using the aromatic or heteroaromatic halogenated methyl sulfides listed below in Tables 1, 2 and 3 as the starting material in place of the compound used in Example 1, whereby the corresponding aromatic or heteroaromatic thiols were produced.

TABLE 1

| Ex. | Starting Material | Reaction Product | Yield (%) |
|---|---|---|---|
| 2 | 2-Chlorophenyl dichloromethyl sulfide | 2-Chlorothiophenol | 93.8 |
| 3 | 2-Chlorophenyl trichloromethyl sulfide | 2-Chlorothiophenol | 93.5 |
| 4 | 2,4-Dichlorophenyl dichloromethyl sulfide | 2,4-Dichlorothiophenol | 94.7 |
| 5 | 2,5-Dichlorophenyl dichloromethyl sulfide | 2,5-Dichlorothiophenol | 94.6 |
| 6 | 3,5-Dichlorophenyl dichloromethyl sulfide | 3,5-Dichlorothiophenol | 93.1 |
| 7 | 2,6-Dichlorophenyl dichloromethyl sulfide | 2,6-Dichlorothiophenol | 95.0 |
| 8 | 4-Bromophenyl dichloromethyl sulfide | 4-Bromothiophenol | 93.3 |
| 9 | 4-Bromophenyl trichloromethyl sulfide | 4-Bromothiophenol | 94.5 |
| 10 | 1,4-Di(dichloromethylthio)benzene | 1,4-Benzenedithiol | 92.5 |
| 11 | 1,4-Di(trichloromethylthio)benzene | 1,4-Benzenedithiol | 92.2 |
| 12 | 1,2-Di(dichloromethylthio)benzene | 1,2-Benzenedithiol | 91.4 |
| 13 | 1,2-Di(dichloromethylthio)-4-butylbenzene | 4-Butyl-1,2-benzene-dithiol | 91.8 |
| 14 | 4-Cyanophenyl dichloromethyl sulfide | 4-Cyanothiophenol | 94.5 |
| 15 | 2-Cyanophenyl dichloromethyl sulfide | 2-Cyanothiophenol | 94.6 |

TABLE 2

| Ex. | Starting Material | Reaction Product | Yield (%) |
|---|---|---|---|
| 16 | 2-Cyanophenyl trichloromethyl sulfide | 2-Cyanothiophenol | 95.1 |
| 17 | 4-Methylphenyl dichloromethyl sulfide | 4-Methylthiophenol | 93.8 |
| 18 | 4-Hydroxyphenyl dichloromethyl sulfide | 4-Hydroxythiophenol | 94.2 |
| 19 | 4-Acetylphenyl dichloromethyl sulfide | 4-Acetylthiophenol | 92.4 |
| 20 | 4-Nitrophenyl dichloromethyl sulfide | 4-Nitrothiophenol | 94.9 |
| 21 | 2-Aminophenyl dichloromethyl sulfide | 2-Aminothiophenol | 94.2 |
| 22 | 4-(Dichloromethylthio)benzoic acid | 4-Mercaptobenzoic acid | 93.6 |
| 23 | 4-(Trichloromethylthio)benzoic acid | 4-Mercaptobenzoic acid | 94.2 |
| 24 | 4-Dichloromethylbenzenesulfonic acid | 4-Mercaptobenzenesulfonic acid | 91.5 |
| 25 | 2-Cyano-3-chlorophenyl dichloromethyl sulfide | 2-Cyano-3-chlorothiophenol | 93.5 |
| 26 | 4-Carbamoylphenyl dichloromethyl sulfide | 4-Carbamoylthiophenol | 94.1 |
| 27 | 4,4'-(Dichloromethylthio)diphenyl sulfide | 4,4'-Thiodibenzenethiol | 91.9 |
| 28 | 4,4'-(Trichloromethylthio)diphenyl sulfide | 4,4'-Thiodibenzenethiol | 92.9 |
| 29 | 4,4'-(Dichioromethylthio)diphenyl ether | 4,4'-Oxydibenzenethiol | 92.1 |

TABLE 3

| Ex. | Starting Material | Reaction Product | Yield (%) |
|---|---|---|---|
| 30 | 4-(Phenylthio)phenyl dichloromethyl sulfide | 4-(Phenylthio)benzenethiol | 95.2 |
| 31 | 4-(Phenylsulfonyl)phenyl dichloromethyl sulfide | 4-(Phenylsulfonyl)benzenethiol | 92.9 |
| 32 | 2-Pyridyl dichloromethyl sulfide | 2-Pyridinethiol | 93.1 |
| 33 | 2-Pyridyl trichloromethyl sulfide | 2-Pyridinethiol | 94.1 |
| 34 | 4-Pyridyl dichloromethyl sulfide | 4-Pyridinethiol | 93.3 |
| 35 | 2-Thienyl dichloromethyl sulfide | 2-Mercaptothiophene | 92.1 |
| 36 | 1-Naphthyl dichloromethyl sulfide | 1-Naphthalenethiol | 94.5 |
| 37 | 1-Naphthyl trichloromethyl sulfide | 1-Naphthalenethiol | 95.2 |
| 38 | 2-Naphthyl dichloromethyl sulfide | 2-Naphthalenethiol | 94.8 |
| 39 | 2-Pyrazyl dichloromethyl sulfide | 2-Mercaptopyrazine | 93.6 |
| 40 | 4-Triazyl dichloromethyl sulfide | 4-Mercaptotriazole | 94.7 |
| 41 | 2-Oxazyl dichloromethyl sulfide | 2-Mercaptooxazole | 92.8 |
| 42 | 4-Isothiazyl dichloromethyl sulfide | 4-Mercaptoisothiazole | 93.1 |

EXAMPLE 43

A 1-liter, 4-necked flask equipped with a stirrer, thermometer, condenser and gas inlet tube was charged with 227.5 g (1.00 mole) of 4-chlorophenyl dichloromethyl sulfide, 50 g of water and 500 g of methanol. The mixture was heated to 70° C. for 5 hours to complete hydrolysis. After completion of the reaction, 357 g (1.05 moles) of 10% aqueous solution of hydrogen peroxide was added dropwise at 40° C. over a period of 1 hour. The mixture was stirred for 1 hour at the same temperature. The precipitated crystals were filtered, giving 134.7 g of 4,4'-dichlorodiphenyl disulfide in a yield of 93.9% based on 4-chlorophenyl dichloromethyl sulfide.

EXAMPLE 44

The same procedure as in Example 43 was carried out with the exception of using 2-cyanophenyl dichloromethyl sulfide in place of 4-chlorophenyl dichloromethyl sulfide as an aromatic or heteroaromatic halogenated methyl sulfide as the starting material, giving 2,2'-dicyanodiphenyl disulfide in a yield of 92.1% based on 2-cyanophenyl dichloromethyl sulfide.

EXAMPLE 45

The same procedure as in Example 43 was carried out with the exception of using 4-bromophenyl trichloromethyl sulfide in place of 4-chlorophenyl dichloromethyl sulfide as an aromatic or heteroaromatic halogenated methyl sulfide as the starting material, giving 4,4'-dibromodiphenyl disulfide in a yield of 90.3% based on 4-bromophenyl trichloromethyl sulfide.

EXAMPLE 46

A 1-liter, 4-necked flask equipped with a stirrer, thermometer, condenser and dropping funnel was charged with 158.5 g (1.00 mole) of 4-chlorothioanisole and 300 g of monochlorobenzene. Chlorine (149.1 g, 2.1 moles) was blown into the mixture at 5° C. over 2 hours. Thereafter 50 g of water and 500 g of methanol were added, and the mixture was heated at 70° C. for 5 hours to complete hydrolysis. After completion of the reaction, water was added to separate the oil layer, and monochlorobenzene was distilled off. Thereafter, distillation gave 133.3 g of 4-chlorothiophenol. The yield based on 4-chlorothioanisole was 92.2%.

EXAMPLES 47 TO 70

The same procedure as in Example 46 was carried out with exception of using the aromatic or heteroaromatic thioanisoles as the starting material listed below in Tables 4 and 5 in place of the compound used in Example 46, whereby the corresponding aromatic or heteroaromatic thiols were produced.

TABLE 4

| Ex. | Starting Material | Reaction Product | Yield (%) |
|---|---|---|---|
| 47 | 2-Chlorothioanisole | 2-Chlorothiophenol | 91.5 |
| 48 | 2,4-Dichlorothioanisole | 2,4-Dichlorothiophenol | 92.4 |
| 49 | 2,5-Dichlorothioanisole | 2,5-Dichlorothiophenol | 92.1 |
| 50 | 3,5-Dichlorothioanisole | 3,5-Dichlorothiophenol | 93.0 |
| 51 | 2,6-Dichlorothioanisole | 2,6-Dichlorothiophenol | 91.5 |
| 52 | 4-Bromothioanisole | 4-Bromothiophenol | 92.5 |
| 53 | 1,4-(Dimethylthio)benzene | 1,4-Benzenedithiol | 90.0 |
| 54 | 1,2-(Dimethylthio)benzene | 1,2-Benzenedithiol | 89.5 |
| 55 | 4-Cyanothioanisole | 4-Cyanothiophenol | 92.5 |
| 56 | 2-Cyanothioanisole | 2-Cyanothiophendl | 92.4 |
| 57 | 4-Hydroxythioanisole | 4-Hydroxythiophenol | 93.5 |
| 58 | 4-Acetylthioanisole | 4-Acetylthiophenol | 90.8 |
| 59 | 4-Nitrothioanisole | 4-Nitrothiophenol | 91.5 |

TABLE 5

| Ex. | Starting Material | Reaction Product | Yield (%) |
|---|---|---|---|
| 60 | 4-(Methylthio)benzoic acid | 4-Mercaptobenzoic acid | 92.4 |
| 61 | 4-Methylthiobenzenesulfonic acid | 4-Mercaptobenzenesulfonic acid | 89.2 |
| 62 | 4-Carbamoylthioanisole | 4-Carbamoylthiophenol | 89.8 |
| 63 | 4,4'-(Dimethylthio)diphenyl sulfide | 4,4'-Thiodibenzenethiol | 89.9 |
| 64 | 4,4'-(Dimethylthio)diphenyl ether | 4,4'-Oxydibenzenethiol | 90.4 |
| 65 | 4-(Phenylthio)thioanisole | 4-(Phenylthio)benzenethiol | 91.0 |
| 66 | 4-(Phenylsulfonyl)thioanisole | 4-(Phenylsulfonyl)-benzenethiol | 90.5 |
| 67 | 2-Pyridylthioanisole | 2-Pyridinethiol | 92.5 |
| 68 | 4-Pyridylthioanisole | 4-Pyridinethiol | 93.0 |
| 69 | 2-Thienylthioanisole | 2-Mercaptothiophene | 92.0 |
| 70 | 1-Naphthylthioanisole | 1-Naphthalenethiol | 95.1 |

EXAMPLE 71

A 1-liter, 4-necked flask equipped with a stirrer, thermometer, condenser and dropping funnel was charged with 158.5 g (1.00 mole) of 4-chlorothioanisole and 300 g of monochlorobenzene. Chlorine (149.1 g, 2.1 moles) was blown into the mixture at 5° C. over 2 hours. Thereafter 50 g of water and 500 g of methanol were added, and the mixture was heated at 70° C. for 5 hours to complete hydrolysis. After completion of the reaction, 357 g (1.05 moles) of 10% aqueous solution of hydrogen peroxide was added dropwise at 40° C. over a period of 1 hour. The mixture was stirred for 1 hour at the same temperature. The precipitated crystals were filtered, giving 132.0 g of 4,4'-dichlorodiphenyl disulfide in a yield of 92.0% based on 4-chlorothioanisole.

EXAMPLE 72

The same procedure as in Example 71 was carried out with the exception of using 2-cyanothioanisole in place of 4-chlorothioanisole as an aromatic or heteroaromatic thioanisole as the starting material, giving 2,2'-dicyanodiphenyl disulfide in a yield of 92.1% based on 2-cyanothioanisole.

EXAMPLE 73

A 1-liter, 4-necked flask equipped with a stirrer, thermometer, condenser and dropping funnel was charged with 158.5 g (1.00 mole) of 4-chlorothioanisole and 300 g of monochlorobenzene. Chlorine (149.1 g, 2.1 moles) was blown into the mixture at 5° C. over 2 hours. The reaction mixture was washed with water and dehydrated with magnesium sulfate, followed by distilling off monochlorobenzene. Thereafter, distillation gave 220.3 g of 4-chlorophenyl dichloromethyl sulfide in a yield of 96.8% based on 4-chlorothioanisole.

What is claimed is:

1. A process for preparing a heteroaromatic thiol represented by formula (2), said process comprising the step of hydrolyzing a heteroaromatic halogenated methyl sulfide represented by formula (1):

Ar—(SCH$_{3-m}$X$_m$)$_n$ (1)

Ar—(SH)$_n$ (2)

wherein Ar is a heteroaromatic ring, X is a halogen atom, m is an integer of 1 to 3, and n is 1 or 2.

2. The process according to claim 1, wherein X in the formula (1) is chlorine.

3. The process according to claim 1, wherein m in the formula (1) is 2 or 3.

4. The process according to claim 1, wherein the hydrolysis is conducted in the presence of an acid.

5. The process according to claim 4, wherein the acid is hydrochloric acid or sulfuric acid.

6. The process according to claim 1, wherein the hydrolysis is conducted in the presence of a lower alcohol.

7. The process according to claim 6, wherein the lower alcohol is methanol.

8. The process according to claim 1, wherein Ar in formulas (1) and (2) is selected from the group consisting of a pyridine ring, pyrazole ring, pyrazine ring, triazole ring, oxazole ring, isooxazole ring, thiazole ring, isothiazole ring, thiophene ring, benzothiophene ring, furan ring, benzofuran ring, pyrrole ring, and indole ring.

9. A process for preparing a heteroaromatic disulfide represented by formula (3), said process comprising the steps of hydrolyzing a heteroaromatic halogenated methyl sulfide represented by formula (1), and oxidizing the reaction mixture:

$$Ar—(SCH_{3-m}X_m)_n \quad (1)$$

$$((HS)_{n-1}—Ar—S)_2— \quad (3)$$

wherein Ar is a heteroaromatic ring, X is a halogen atom, m is an integer of 1 to 3, and n is 1 or 2.

10. The process according to claim 9, wherein X in the formula (1) is chlorine.

11. The process according to claim 9, wherein m in the formula (1) is 2 or 3.

12. The process according to claim 9, wherein the hydrolysis is conducted in the presence of an acid.

13. The process according to claim 12, wherein the acid is hydrochloric acid or sulfuric acid.

14. The process according to claim 9, wherein hydrolysis is conducted in the presence of a lower alcohol.

15. The process according to claim 14, wherein the lower alcohol is methanol.

16. The process according to claim 9, wherein Ar in formulas (1) and (3) is selected from the group consisting of a pyridine ring, pyrazole ring, pyrazine ring, triazole ring, oxazole ring, isooxazole ring, thiazole ring, isothiazole ring, thiophene ring, benzothiophene ring, furan ring, benzofuran ring, pyrrole ring, and indole ring.

17. A process for preparing a heteroaromatic halogenated methyl sulfide represented by formula (1), said process comprising halogenating a heteroaromatic methyl sulfide represented by formula (4):

$$Ar—(SCH_3)_n \quad (4)$$

$$Ar—(SCH_{3-m}X_m)_n \quad (1)$$

wherein Ar is a heteroaromatic ring, X is a halogen atom, m is an integer of 1 to 3, and n is 1 or 2.

18. The process according to claim 17 wherein the heteroaromatic methyl sulfide is halogenated by chlorine.

19. The process according to claim 17, wherein m in the formula (1) is 2 or 3.

20. The process according to claim 1, further comprising, prior to the hydrolyzing step, halogenating a heteroaromatic methyl sulfide represented by formula (4) to give heteroaromatic halogenated methyl sulfide used in the hydrolyzing step:

$$Ar—(SCH_3)_n \quad (4)$$

wherein Ar is as defined in formula (1).

21. The process according to claim 9, further comprising, prior to the hydrolyzing step, halogenating a heteroaromatic methyl sulfide represented by formula (4) to give the heteroaromatic halogenated methyl sulfide used in the hydrolyzing step:

$$Ar—(SCH_3)_n \quad (4)$$

wherein Ar is as defined in formula (1).

22. The process according to claim 9, wherein the oxidation is conducted using a hydrogen peroxide.

23. The process according to claim 21, wherein the oxidation is conducted using a hydrogen peroxide.

* * * * *